United States Patent [19]

Sapper

[11] Patent Number: 4,695,304

[45] Date of Patent: Sep. 22, 1987

[54] SEPARATION OF $CO_2$ FROM A GASEOUS MIXTURE

[75] Inventor: Rainer Sapper, Neuried, Fed. Rep. of Germany

[73] Assignee: Linde Aktiengesellschaft, Wiesbaden, Fed. Rep. of Germany

[21] Appl. No.: 743,727

[22] Filed: Jun. 12, 1985

[30] Foreign Application Priority Data

Jun. 14, 1984 [DE] Fed. Rep. of Germany ....... 3422158
May 3, 1985 [DE] Fed. Rep. of Germany ....... 3515949

[51] Int. Cl.$^4$ .................................................. F24J 3/02
[52] U.S. Cl. ....................................... 62/27; 62/32; 62/42
[58] Field of Search ................... 62/11, 20, 23, 24, 27, 62/32, 42

[56] References Cited

U.S. PATENT DOCUMENTS

| | | | |
|---|---|---|---|
| 3,656,312 | 4/1972 | Streich | 62/23 |
| 3,874,184 | 4/1975 | Harper et al. | 62/23 |
| 3,983,711 | 10/1976 | Solomon | 62/28 |
| 4,043,770 | 8/1977 | Jakob | 62/23 |
| 4,115,086 | 9/1978 | Jordan et al. | 62/18 |
| 4,149,864 | 4/1979 | Eakman et al. | 62/11 |
| 4,256,476 | 3/1981 | Van Baush | 62/23 |
| 4,311,495 | 1/1982 | Styring, Jr. | 62/17 |
| 4,336,044 | 6/1982 | Barker et al. | 62/17 |
| 4,350,511 | 9/1982 | Holmes et al. | 62/17 |
| 4,428,759 | 1/1984 | Ryan et al. | 62/17 |
| 4,444,571 | 4/1984 | Matson | 55/49 |
| 4,488,890 | 12/1984 | Foerg et al. | 62/17 |
| 4,559,069 | 12/1985 | Becker | 62/23 |
| 4,563,202 | 1/1986 | Yao et al. | 62/17 |
| 4,566,886 | 1/1986 | Fabian et al. | 62/11 |
| 4,595,404 | 6/1986 | Ozero et al. | 62/18 |

Primary Examiner—Ronald C. Capossela
Attorney, Agent, or Firm—Millen & White

[57] ABSTRACT

For the separation of $CO_2$ from a gaseous mixture containing $CO_2$ and $C_1$–$C_6$ hydrocarbons, the gaseous mixture to be fractionated is separated in a first fractionating stage into an overhead fraction containing substantially all of the $C_1$ and $C_2$ hydrocarbons as well as $CO_2$ in a molar ratio $CO_2/C_2$ of 2:1 to 3.5:1, and into a bottoms fraction containing the remainder of $CO_2$ and the $C_{3+}$ hydrocarbons. The fraction containing $CO_2/C_{3+}$ hydrocarbons is further fractionated, preferably in two serially connected rectification columns, into $CO_2$ and $C_{3+}$ hydrocarbon fractions.

27 Claims, 1 Drawing Figure

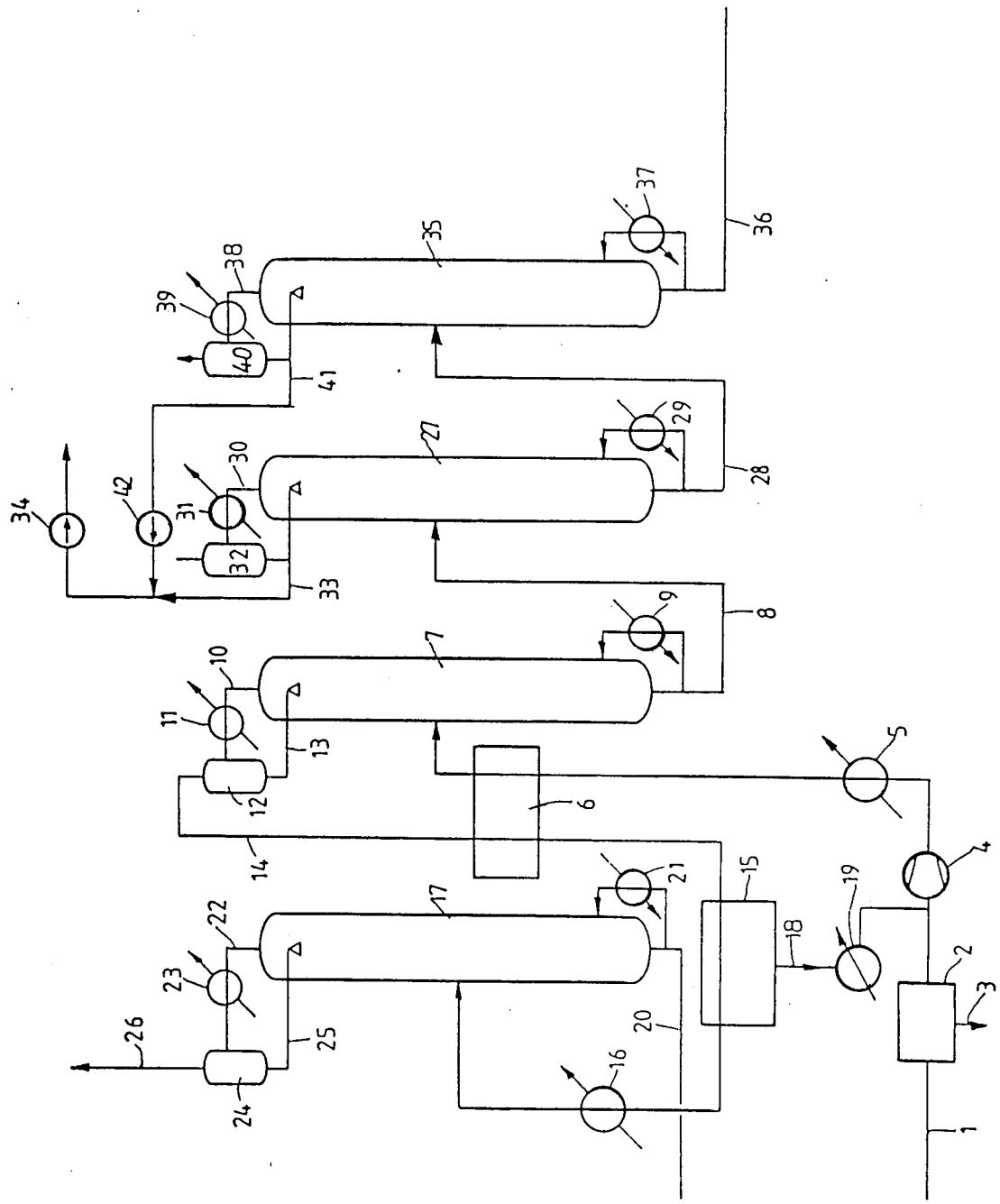

SEPARATION OF CO₂ FROM A GASEOUS MIXTURE

BACKGROUND OF THE INVENTION

This invention relates to a distillation process for the separation of $CO_2$ from a gaseous mixture containing $CO_2$ and light hydrocarbons as well as to an apparatus for conducting such a process.

In the distillation of light hydrocarbons, especially $C_1$ to $C_6$ hydrocarbons having a relatively high proportion of $CO_2$, e.g., more than 5 molar %, a problem is encountered because of the propensity of $CO_2$ to condense in solid form. This problem is particularly evident in the processing of $CO_2$-rich natural gases, i.e., natural gases having a $CO_2$ content of more than about 5%, or in tertiary oil recovery where $CO_2$ under high pressure is injected into oil bearing formations. In the latter case, besides petroleum, an accompanying gas containing light hydrocarbons is obtained which can contain, for example, between 5 and 95% $CO_2$; usually, the $CO_2$ content of this gas will gradually increase during the course of the tertiary oil recovery process from a relatively low value to a very high value while the amount of light hydrocarbons contained in the gas remains essentially constant. Whereas $CO_2$ is generally separated from $CO_2$-rich natural gases because it is an undesirable impurity, in the case of tertiary oil recovery, $CO_2$ is a desirable product stream which is reinjected into the formation under high pressure.

A conventional process for separating $CO_2$ from light hydrocarbons provides for separation of a $C_1$ fraction from the mixture in a first fractionating stage, and fractionation of the remaining $C_{2+}$—$CO_2$ mixture in a further fractionating stage into $CO_2$ and a $C_{2+}$ fraction. However, this fractionation process is beset with a number of difficulties. Thus, when separating $CH_4$ and $CO_2$ under conditions normally prevailing during demethanization, solid $CO_2$ deposits are formed in the fractionating column. In addition, during the subsequent separation of $CO_2$ and $C_{2+}$ hydrocarbons, $CO_2$ forms an azeotrope with ethane at a $CO_2/C_2$ molar ratio of about 2:1; consequently, further fractionation of this azeotrope by distillation requires the use of a special technique to change the relative volatilities of the $CO_2$ and $C_2$. Such a special technique is disclosed, for example in the so-called Ryan-Holmes process (Hydrocarbon Processing, May 1982, p. 131), wherein additives are introduced to prevent solid $CO_2$ deposition or to break the $CO_2/C_2$ azeotrope.

Unfortunately, the Ryan-Holmes process is excessively energy-intensive because in the fractionating stages, it is necessary to cool not only tne entire amount of gas to be fractionated to the respective operating temperatures in the two fractionating columns, but also the solvent additive as well. This leads to expensive cooling cycles and high operating costs, especially during the demethanization step which is conducted at relatively low temperatures (on the order of $-80°$ to $-90°$ C.).

SUMMARY OF THE INVENTION

An object of one aspect of the invention, therefore, is to provide an improved process of the type discussed above.

An object of another aspect of the invention is to provide such a process having low operating costs and permitting, without requiring a relatively high outlay for apparatus, the fractionation of gaseous mixtures of the aforedescribed composition.

An object of a still further aspect is to provide a combination of apparatus features especially adapted for the above processes.

Upon further study of the specification and appended claims, further objects and advantages of this invention will become apparent to those skilled in the art.

To attain these objects, a process is provided comprising: (a) separating the gaseous mixture to be fractionated, in a first fractionating stage, into an overhead fraction containing substantially all of the $C_1$ and $C_2$ hydrocarbons and a portion of the $CO_2$, preferably minor, and into a bottom fraction containing substantially all the $C_{3+}$ hydrocarbons and a portion, preferably the major portion of the $CO_2$; and (b) in a second fractionating stage, fractionating the bottom fraction into a $CO_2$ fraction and into a $C_{3+}$ hydrocarbon fraction. In certain cases, for example wherein the $C_{3+}$ content is negligible, step (b) may be omitted.

In the process of this invention, the first fractionating stage is conducted so as to obtain an overhead stream containing substantially all of both methane and ethane as contrasted with the conventional process wherein a methane overhead and a $CO_2/C_{2+}$ bottoms are obtained. The overhead product of the first fractionating stage of this invention not only contains the $C_1$ and $C_2$ hydrocarbons, but also contains a portion of the $CO_2$ from the gaseous mixture, since unavoidably the portion of the $CO_2$ corresponding to the $CO_2/C_2$ azeotrope is discharged overhead together with the $C_1$-$C_2$ fraction. This proportion of $CO_2$ in the overhead is essentially independent of the $CO_2$ content in the gaseous mixture to-be-fractionated and depends only on the $C_2$ content of the gaseous mixture. Therefore, this $CO_2$ loss is relatively minor in case of a very high $CO_2$ content and/or low $C_2$ content in the gaseous mixture to-be-fractionated, whereas it is higher with gases to-be-fractionated having a relatively low $CO_2$ content and/or a relatively high $C_2$ content in a relationship to the total $CO_2$ remaining in the bottoms fraction.

In order to eliminate these losses and, in particular, to be able to conduct the process of this invention under favorable conditions with relatively low $CO_2$ contents, a preferred embodiment of the invention comprises the separation of the overhead from the first fractionating stage, in preferably a non-distillative process to recover a substantial quantity of substantially the entire $CO_2$ which can then be reintroduced same into the gaseous mixture to be fractionated. This yields not only a $CO_2$-free $C_1$-$C_2$ fraction, but also such a $CO_2$ enrichment in the gaseous mixture to be fractionated that there is always more $CO_2$ than required for the $CO_2/C_2$ azeotrope. Thus, $CO_2$ contained in the raw gas can always be withdrawn as a bottoms fraction from the first fractionating stage. The amount of $CO_2$ that is recycled is approximately two times of the amount of $C_2$ or more, even up to e.g. ten times of the amount of $C_2$ if it is profitable to the process.

Separation of the $CO_2$ from the overhead product from the first fractionating stage can be conducted by any conventional unit operation, for example by scrubbing or by semipermeable membrane separation.

According to this invention, the $CO_2/C_2$ azeotrope in the first fractionation stage is approached from the $CO_2$ side. Thus, the fractionating stage is conducted at temperatures substantially above those very cold temperatures used in the first fractionation stage of the conventional Ryan-Holmes process.

The raw gas introduced into the first fractionating stage is cooled, in the process of this invention, to a temperature on the order of −5° to −20° C., preferably −10° to −15° C. Lower temperatures are required only in an optional follow-on $C_1/C_2$ separation. However, in the latter separation step, the amount of gas to be cooled is already substantially smaller than in the prior art process since the $CO_2$ has already been separated from the $C_1$–$C_2$ components. Consequently, an important advantage of this invention is that the refrigeration power required for the process is considerably reduced.

As implied above, in a preferred further development of the process of this invention, a $CO_2/C_2$ ratio of at least 2:1 (the azeotrope composition) is maintained in the overhead fraction of the first fractionating stage. This means that the composition in the overhead of the first fractionating stage will always be on the $CO_2$ side of the $CO_2/C_2$ azeotrope. Since, on the other hand, the $CO_2$ proportion in the overhead fraction should be at a minimum in order to keep the $CO_2$ losses as small as possible, and to lower the load in any optional subsequent $CO_2$ separation step, a $CO_2/C_2$ molar ratio of at most 3.5:1 is preferably maintained, thereby providing a preferred $CO_2:C_2$ molar range in the overhead of above 2:1 up to 3.5:1, more preferably 2.5:1 to 3:1.

According to the invention, the bottoms fraction from the first fractionating stage is generally fractionated in a further fractionating stage into a $CO_2$ fraction and into a $C_{3+}$ hydrocarbon fraction. It is especially advantageous, according to a further preferred embodiment of the process of this invention, for this further fractionating stage to comprise two serially connected rectification columns. In this way, in the first rectification column, an overhead fraction is obtained containing a portion of the $CO_2$ along with a bottoms fraction containing the residual $CO_2$ and the $C_{3+}$ hydrocarbons; then in the second rectification column the $CO_2/C_{3+}$ fraction is fractionated into a $CO_2$ fraction and a $C_{3+}$ fraction. This particular method of operation is economically important especially where there is a high $CO_2$ molar content in the bottoms fraction from the first fractionating stage, i.e. on the order of 90% and more.

The process of this invention is suitable for processing gases rich in $CO_2$, i.e. gases having a $CO_2$ molar content of more than 5%, especially more than 25% $CO_2$, and is utilized with special advantage with gases having more than 40% $CO_2$ or more than 50% $CO_2$. In this connection, the $CO_2$ content can be even exceedingly high, e.g., up to 95% of the gaseous mixture. The process is also very suitable for the processing gaseous mixtures having widely fluctuating $CO_2$ proportions, for example rising from initially relatively low $CO_2$ proportions; e.g., 20%, to high $CO_2$ proportions, e.g., 90%.

Apparatus for conducting the process of this invention comprises a first fractionating means connected to a raw gas conduit, a discharge conduit in communication with said first fractionating means for removing an overhead product, non-distillative separation means in communication with said discharge conduit for separating $CO_2$ from said overhead product. The non-distillative separation facility preferably contains conventional semi-permeable membranes.

BRIEF DESCRIPTION OF FIGURE

The invention as well as further details of the invention will be described in greater detail with reference to the attached FIGURE which is a schematically illustrated flow chart of a preferred embodiment of this invention.

DETAILED DESCRIPTION OF FIGURE

A raw gas mixture 1, derived, for example, from tertiary oil recovery, has the following typical data:

| | |
|---|---|
| $CO_2$ | 92 mol % |
| $CH_4$ | 2 mol % |
| $C_2H_6$ | 2 mol % |
| $C_{3+}$ | 4 mol % |
| $H_2S$ + $N_2$ respectively below | 0.1 mol % |
| Temperature | 303 K. |
| Pressure | 1 bar |

The $H_2S$ contained in the raw gas is preferably removed, for example, in a Stretford process facility 2 and removed via a conduit 3. The remaining, essentially $H_2S$-free raw gas mixture is combined with $CO_2$ fed via a conduit 18, the quantity of $CO_2$ added being about 6 moles per 100 moles of raw gas. Subsequently the raw gas is compressed in a compressor 4 to about 40 bar and cooled in a cooler 5 as well as in a heat exchanger 6. The gaseous mixture is then introduced into a first fractionating column 7. A temperature of about −10° to −13° C. is maintained at the head of the fractionating column 7, the temperature being substantially higher than the temperature at which solid precipitation of $CO_2$ occurs (approximately at −60° C.). The ratio of $CO_2/C_2$ in the overhead stream is about 2.9, i.e. it is on the $CO_2$ side of the azeotropic composition which at 40 bar is about 69 mol-%.

A liquid bottoms fraction formed in the fractionating column 7 and removed via conduit 8 has the following characteristics:

| | |
|---|---|
| $CO_2$ | 96 mol % |
| $C_{3+}$ | 4 mol % |
| $C_2$ below | 0.1 mol % |
| Temperature | 280 K. |
| Pressure | 40 bar |

A portion of the bottom fraction is heated in reboiler 9 and returned into the fractionating column.

Via a conduit 10, a gaseous overhead fraction is removed from the head of the fractionating column 7; this fraction contains the $C_1$ and $C_2$ hydrocarbons, as well as part of the $CO_2$ and has the following composition:

| | |
|---|---|
| $CO_2$ | 55 mol % |
| $CH_4$ | 25 mol % |
| $C_2H_6$ | 19 mol % |
| $N_2$ below | 1 mol % |
| Temperature | 259 K. |
| Pressure | 40 bar |

The amount of $CO_2$ is substantially independent of the $CO_2$ quantity in the raw gas mixture, but is instead dependent on the $CO_2/C_2$ ratio prevailing in the head of this column, whereby the $C_2$ proportion in turn determines the amount of $CO_2$ withdrawn in the overhead.

The overhead fraction is cooled and partially condensed in a condenser 11. The condensate is separated in a phase separator 12 and returned as reflux into the fractionating column 7 via a conduit 13. The gaseous proportion, after being heated in heat exchanger 6 from 259 K. to 290 K., is fed into a diffusion unit 15 containing semipermeable membranes. By means of diffusion, the $CO_2$ contained in the head fraction is separated and withdrawn from the downstream side of the membranes (conduit 18). Since, as mentioned above, the total amount of gas in conduit 14 is essentially constant even with a varying $CO_2$ content in the raw gas mixture, the dimensioning of the diffusion facility 15 is simplified. After being heated in a heat exchanger 19 to 290 K., the $CO_2$ is recycled into the raw gas mixture 1. This latter step of membrane separation makes it possible for the $CO_2/C_2$ ratio in the first fractionating column 7 to always be maintained higher than the azeotropic composition. This is of particular advantage when the $CO_2$ concentration in the raw gas is either initially low or fluctuates to low concentrations. The type of semipermeable membrane used can be of the spiral wound type or consisting of hollow fibers.

The residual substantially $CO_2$-free fraction is cooled in a cooler 16 and introduced into a second fractionating column 17. This fraction has the following characteristics (upstream of cooler 16):

| | |
|---|---|
| $CH_4$ | 52 mol % |
| $C_2H_6$ | 44 mol % |
| $N_2$ | 2 mol % |
| $CO_2$ | 2 mol % |
| Temperature | 280 K. |
| Pressure | 40 bar |

In fractionating column 17, a $C_1$ overhead fraction is discharged via a conduit 22, and a $C_2$ bottom fraction is discharged via a conduit 20. The overhead fraction is partially condensed in a condenser 23, separated in a separator 24 and introduced via a conduit 25 into the fractionating column 17 as reflux. The $C_1$ proportion that remains in the gaseous phase is withdrawn via a conduit 26.

A portion of the bottoms liquid is branched off from conduit 20 and, after being heated in reboiler 21, is returned into the fractionating column 17.

The liquid bottoms fraction from fractionating column 7 is introduced into a fractionating column 27 where a portion of the $CO_2$ is separated overhead. The $CO_2$ removed via a conduit 30 is either partially or completely condensed in a condenser 31. In the case of partial condensation, the proportion that remains in the gaseous phase is separated in a separator 32 while the liquefied proportion is, in part, introduced as reflux liquid into the fractionating column 27. In case of total condensation, the liquefied $CO_2$ is withdrawn via conduit 33 at a purity of 99.8%. This liquefied $CO_2$ is brought to a higher pressure, for example by means of a pump 34, and pumped back into a well hole for tertiary oil recovery.

A liquid mixture withdrawn in conduit 28 from the bottom of the fractionating column 27 has the following characteristics:

| | |
|---|---|
| $CO_2$ | 50 mol % |
| $C_{3+}$ | 50 mol % |
| $C_2H_6$ about | 0.01 mol % |
| Temperature | 294 K. |
| Pressure | 35 bar |

A portion of the liquid is returned via a reboiler 29 into the fractionating column 27; the remainder is fed into a further fractionating column 35 wherein the residual $CO_2$ is separated overhead in conduit 38 from the $C_{3+}$ bottoms fraction in conduit 36.

The overhead fraction, containing $CO_2$ having a purity of about 99.5%, is either completely or partially condensed in condenser 39. With total liquefaction in condenser 39, a portion of the liquid from tank 40 is introduced as reflux into the column 35, and the remainder is conveyed as a product via conduit 41 by means of a pump 42 to join the liquid product fraction in conduit 33.

A portion of the liquid bottom fraction in conduit 36, containing about 99.9 mol-% of $C_{3+}$ hydrocarbons, is recycled via a reboiler 37 into the fractionating column 35, whereas the remainder is discharged.

Fractionation of fraction 8 in two successive fractionating columns 27 and 35 is economical if the $CO_2$ content in the raw gas is above approximately 90%. In case of lower $CO_2$ concentrations, separation can be conducted in one stage.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the separation of $CO_2$ from a gaseous mixture containing $CO_2$ and at least $C_1$-$C_2$ hydrocarbons, said process comprising separating said gaseous mixture in a first fractionating stage into an overhead fraction containing substantially all the $C_1$ and $C_2$ hydrocarbons and a minor portion of the $CO_2$ and into a bottoms fraction containing the major portion of the $CO_2$.

2. A process according to claim 1, said gaseous mixture further containing at least $C_3$ hydrocarbons, the latter being separated into the bottoms fraction of said first fractionating stage, and further comprising fractionating said bottoms fraction in a second fractionating stage into a $CO_2$ overhead fraction and into a $C_{3+}$ hydrocarbon bottoms fraction.

3. A process according to claim 2, said second fractionating stage comprising two serially connected rectification columns, and separating the liquid bottoms from the first fractionating stage in the first rectification column into an overhead fraction containing a portion of the $CO_2$ and a bottoms fraction containing the remainder of $CO_2$ and the $C_{3+}$ hydrocarbons, and separating the $CO_2/C_{3+}$ bottoms fraction in the second rectification column into a $CO_2$ fraction and a $C_{3+}$ fraction.

4. A process according to claim 3 wherein the molar content of $CO_2$ in the liquid bottoms from the first fractionating stage is over 90 %.

5. A process according to claim 2, wherein the first fractionating stage is conducted so as to maintain a $CO_2/C_2$ molar ratio of at least 2:1 in the overhead fraction of the first fractionating stage.

6. A process according to claim 5 further comprising separating the $CO_2$ in the overhead fraction of the first fractionating stage by a non-distillative separation process.

7. A process according to claim 6, said separation of $CO_2$ from the overhead fraction being conducted by diffusion through a semipermeable membrane.

8. A process according to claim 5, wherein the $CO_2/C_2$ molar range in said overhead ranges from about 2.5:1 to 3:1.

9. A process according to claim 2 further comprising separating the $CO_2$ in the overhead fraction of the first fractionating stage by a non-distillative separation process.

10. A process according to claim 9, said separation of $CO_2$ from the overhead fraction being conducted by diffusion through a semipermeable membrane.

11. A process according to claim 9, further comprising reintroducing the thus-separated $CO_2$ into the gaseous mixture to be fractionated.

12. A process according to claim 1, wherein the first fractionating stage is conducted so as to maintain a $CO_2/C_2$ molar ratio of at least 2:1 in the overhead fraction of the first fractionating stage.

13. A process according to claim 12 further comprising separating the $CO_2$ in the overhead fraction of the first fractionating stage by a non-distillative separation process.

14. A process according to claim 13, said separation of $CO_2$ from the overhead fraction being conducted by diffusion through a semipermeable membrane.

15. A process according to claim 14, further comprising reintroducing the thus-separated $CO_2$ into the gaseous mixture to be fractionated.

16. A process according to claim 15, said $CO_2/C_2$ molar ratio being not higher than 3.5.

17. A process according to claim 12, said $CO_2/C_2$ molar ratio being not higher than 3.5.

18. A process according to claim 3, wherein the $CO_2/C_2$ molar ratio in said overhead fraction ranges from about 2.5:1 to 3:1.

19. A process according to claim 1 further comprising separating the $CO_2$ in the overhead fraction of the first fractionating stage by a non-distillative separation process.

20. A process according to claim 19, said separation of $CO_2$ from the overhead fraction being conducted by diffusion through a semipermeable membrane.

21. A process according to claim 20, further comprising reintroducing the thus-separated $CO_2$ into the gaseous mixture to be fractionated.

22. A process according to claim 19, further comprising reintroducing the thus-separated $CO_2$ into the gaseous mixture to be fractionated.

23. A process according to claim 13, wherein the amount of $CO_2$ reintroduced into the gaseous mixture to be fractionated ranges from about 2 to 10 times the amount of $C_2$ fraction present.

24. A process according to claim 1, wherein the $CO_2$ content of the gaseous mixture ranges from about 5 to 95% $CO_2$.

25. A process according to claim 1, wherein said gaseous mixture contains fluctuating $CO_2$ proportions ranging from about 20 to 90% $CO_2$.

26. A process according to claim 1, wherein said gaseous mixture is introduced into said first fractionating stage at a temperature of $-5°$ to $-20°$ C.

27. A process according to claim 1, wherein said gaseous mixture is introduced into said first fractionating stage at a temperature of $-10°$ to $-15°$ C.

* * * * *